United States Patent [19]

Jonas et al.

[11] Patent Number: 4,568,494

[45] Date of Patent: Feb. 4, 1986

[54] PROCESS FOR THE PREPARATION OF TCNQ COMPLEXES

[75] Inventors: Friedrich Jonas, Aachen; Jürgen Hocker, Bergisch Gladbach, both of Fed. Rep. of Germany

[73] Assignee: Bayer Aktiengesellschaft, Leverkusen-Bayerwerk, Fed. Rep. of Germany

[21] Appl. No.: 651,260

[22] Filed: Sep. 17, 1984

[30] Foreign Application Priority Data

Sep. 30, 1983 [DE] Fed. Rep. of Germany ....... 3335589

[51] Int. Cl.$^4$ .............................................. H01B 1/00
[52] U.S. Cl. .................. 260/396 N; 252/500
[58] Field of Search ................... 252/500; 260/396 N, 260/DIG. 18, 21; 524/911, 910, 913

[56] References Cited

U.S. PATENT DOCUMENTS

| 3,424,698 | 1/1969 | Lupinski | 252/500 |
| 4,293,452 | 10/1981 | Fox et al. | 252/518 |
| 4,374,048 | 2/1983 | Kim et al. | 252/500 |
| 4,478,751 | 10/1984 | Jonas et al. | 252/500 |

OTHER PUBLICATIONS

J. Am. Chem. Soc. 84, 3374–3387, 1962.

Primary Examiner—Josephine L. Barr
Attorney, Agent, or Firm—Connolly and Hutz

[57] ABSTRACT

This invention relates to a process for the preparation of charge transfer complexes containing 7,7,8,8-tetracyanoquinodimethane by the reaction of TCNQ with organic cation iodides or by the reaction of nitrogen-containing heteroaromatic compounds and tertiary amines with $H_2TCNQ$, using smaller quantities of solvent than that required for complete solution of the TCNQ.

5 Claims, No Drawings

PROCESS FOR THE PREPARATION OF TCNQ COMPLEXES

Complex salts of the 7,7,8,8-tetracyano-p-quinodimethane anion (TCNQ)

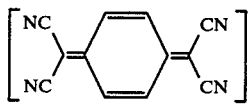

neutral TCNQ and inorganic or organic cations are known as electrically conductive compounds and have acquired great interest in recent times, e.g. for the production of condensers.

These complexes may be prepared by the reaction of TCNQ with organic cation iodides [J. Am. Chem. Soc. 84, 3374–3387 (1962)], e.g.

Reaction scheme I

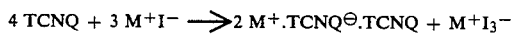

In this reaction, a TCNQ molecule is reduced by iodide to the TCNQ anion with liberation of iodine, which reacts with excess iodide to form the $I_3{}^-$ anion.

Another method consists in the reaction of nitrogen-containing heteroaromatic compounds and tertiary amines with $H_2TCNQ$ (I) and TCNQ, e.g.

Reaction scheme II

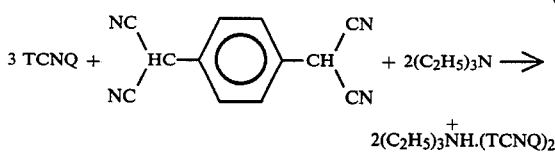

In both processes, the reactants are generally dissolved in suitable solvents, in most cases at elevated temperatures, and the solutions are then combined. The solvent used is in most cases acetonitrile or methylene chloride.

Since TCNQ is very difficult to dissolve in the solvents used, even under heat (solubility in methylene chloride under reflux $\approx 6$ g/l), these processes require the use of large quantities of solvent which must subsequently be worked up. The preparation of TCNQ complex salts with less solvent than that required for solution under reflux does not result in pure products (Comparison Example 1), the reaction of TCNQ being incomplete. Moreover, the complexes are liable to undergo partial decomposition owing to the long reaction time at a high temperature.

It has surprisingly been found that TCNQ complexes can be prepared using small quantities of solvent if the organic cation iodide is present in the solvent while the TCNQ is continuously added and the solvent is recycled (e.g. by means of extraction with a Soxhlet apparatus).

The present invention therefore relates to a process for the preparation of charge transfer complexes containing 7,7,8,8-tetracyanodimethane by means of reaction TCNQ with organic cation iodides or nitrogen-containing heteroaromatic compounds and tertiary amines with $H_2TCNQ$ and TCNQ, which process comprises applying certain solvents in quantities insufficient for complete solution of the TCNQ.

A further advantage of the process according to the invention is that the TCNQ complexes are obtained in the form of very fine needles which are advantageously used to render polymers antistatic (see DE-OS No. 3,005,849), whereas the complexes obtained from the usual method of preparation are not suitable for this purpose.

Suitable solvents for carrying out the process according to the invention include organic solvents, e.g. halogenated hydrocarbons such as methylene chloride, chloroform, carbon tetrachloride, 1,2-dichloroethane or 1,1,2-trichloroethane; acetonitrile; alcohols such as methanol, ethanol or isopropanol; aliphatic ketones such as acetone or methyl ethyl ketone; and acyclic and cyclic ethers, e.g. diethylether or tetrahydrofuran. Solvents having a low boiling point (below 100° C.) are preferred in order to prevent thermal damage to the complex formed.

Solvents having a boiling point below 60° C., e.g. methylene chloride, are particularly preferred.

The solvents may be used in very small quantities, based on the quantity of TCNQ put into the process, but to ensure that the process may be technically feasible to carry out, it is advisable to use at least 10 ml of solvent per gram of TCNQ. The quantity of sovlent used is preferably from 15 to 30 ml of solvent per gram of TCNQ used, but may be higher.

If preparation of the CT complexes is carried out according to Reaction scheme II, the conditions indicated above for TCNQ apply to the sum of TCNQ and $H_2TCNQ$ used. In principle, any organic cation iodides or tertiary amines or N-heteroaromatic compounds are suitable for carrying out the process.

A survey may be found in J. Am. Chem. Soc. 84, 3370 to 3387 (1962).

It is preferred to use cation iodides which are soluble in organic solvents, e.g. N-methyl-quinolinium iodide or N-butyl-isoquinolinium iodide.

Suitable apparatus for carrying out the process (e.g. Thielepae attachment, Soxhlet extractor) are described in Organikum, VEB Verlag der Wissenschaften 1973, pages 66 to 67, but other apparatus allowing for continuous addition of the TCNQ with recycling of the solvent may also be used.

To carry out the process, the cation iodide is introduced into the reaction vessel in a solvent and the TCNQ is introduced into the extractor. Reflux is then maintained until all the TCNQ has gone into solution. The charge transfer complex formed may be isolated simply by suction filtration. The complex is obtained in high yields and with a high degree of purity.

The complexes obtained by this procedure are eminently suitable for use as antistatic finishes for polymers, e.g. for polyolefins such as polyethylene, polystyrene or polyisoprene; polyvinyl chloride; polyamides such as polyamide-6,6; polyesters such as polyethylene terephthalate; polycarbonates, polyacrylonitrile, copolymers of acrylonitrile, butadiene and styrene (ABS), polyvinyl acetate, cellulose esters such as cellulose acetate, or polyurethanes.

EXAMPLES

Comparison Example 1

27.0 g of N-methyl-quinolinium iodide, 27.2 g of TCNQ and 500 ml of methylene chloride are stirred under reflux in a stirrer apparatus for 24 hours. The reaction product is then suction-filtered and dried. The product contains susbtantial quantities of unreacted TCNQ which is visible as yellow crystals.

Comparison Example 2

27.0 g of N-methyl-quinolinium iodide are dissolved under reflux in 300 ml of acetonitrile. To this solution is added a boiling solution of 27.2 g of TCNQ in 1800 ml of acetonitrile. The complex which precipitates on cooling is suction-filtered and dried.

Example 1

10.8 g of N-isopropyl-isoquinolinium iodide are dissolved in 200 ml of methylene chloride in a stirrer apparatus with Soxhlet attachment. 16.3 g of TCNQ introduced into the Soxhlet attachment are continuously extracted under reflux. The reaction is completed when all the TCNQ has been dissolved out. The precipitated complex is suction-filtered, washed with a small quantity of methylene chloride and dried. 22.3 g=96% of the theoretical yield of the CT complex having the following composition are obtained:

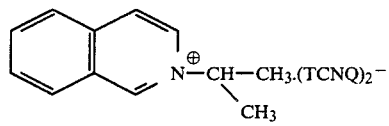

$C_{36}H_{22}N_9$ (580) Calc. 74.5% C, 3.8% H, 21.7% N; Found 74.3% C, 4.0% H, 21.7% N.

Example 2

27.6 g of n-octyl-triphenyl-phosphonium iodide, 10.2 g of TCNQ and 150 ml of methylene chloride are reacted and worked up as described in Example 1.

17.6 g=90% of the theoretical yield of CT complex having the following composition is obtained:

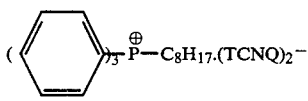

$C_{50}H_{40}N_8P$ (783) Calc. 76.6% C, 5.1% H, 14.3% N; Found 76.2% C, 4.8% H, 14.7% N.

Example 3

18.1 g of N-n-butyl-isoquinolinium iodide, 16.3 g of TCNQ and 200 ml of methylene chloride are reacted as described in Example 1.

21 g=90% of the theoretical yield of CT complex having the following composition are obtained:

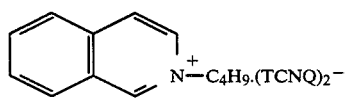

$C_{37}H_{24}N_9$ (594) Calc. 74.8% C, 4.0% H, 21.2% N; Found 74.4% C, 4.2% H, 21.2% N.

Example 4

16.3 g of N-methyl-quinolinium iodide, 16.3 g of TCNQ and 300 ml of methylene chloride are reacted as described in Example 1.

21.2 g=96% of the theoretical yield of CT complex having the following composition are obtained:

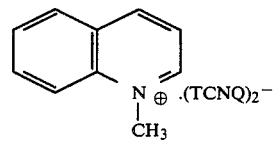

$C_{34}H_{18}N_9$ (552) Calc. 73.9% C, 3.3% H, 22.8% N; Found 73.7% C, 3.9% H, 22.9% N.

Example 5

5.2 g of quinoline (which is our N-heteroaromatic compound and a tertiary amine) are dissolved in 200 ml of methylene chloride in a stirrer apparatus with Soxhlet attachment. 12.2 g of TCNQ and 4.0 g of 7,8-dihydro-TCNQ are introduced into the Soxhlet attachment and the reaction is carried out as described in Example 1.

19.6 g=91% of the theoretical yield of CT complex having the following composition are obtained:

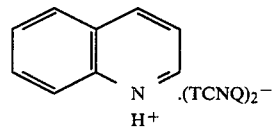

$C_{33}H_{16}N_9$ (538) Calc. 73.6% C, 3.0% H, 23.4% N; Found 73.3% C, 3.2% H, 23.0% N.

Example of practical application 0.2 g of the TCNQ complex of Example 4=Foil A or 0.2 g of the TCNQ complex of Comparison Example 2=Foil B are added to 200 g of a 10% solution in methylene chloride of a commercial polycarbonate having a molar mass of 59 000, and the mixture is stirred until homogeneous distribution of the complex is obtained. The solution is then cast to form a foil which has a thickness of 100 μm after evaporation of solvent, and the surface resistance of the foil is determined.

Foil A $R=1,4 \cdot 10^7 \Omega \times cm$.

Foil B $R=2,3 \cdot 10^{13} \Omega \times cm$ (according to DIN 53 482).

We claim:

1. In an improved process for the preparation of charge transfer complexes containing 7,7,8,8-tetracyanoquinodimethane, which comprises reacting TCNQ with an organic cation iodide or reacting a nitrogen-containing heteroaromatic compound and a tertiary amine with $H_2$TCNQ and TCNQ, the improvement comprises conducting the reaction in the presence of a solvent in an amount less than the quantity required for complete solution of TCNQ and continuously adding TCNQ to the solvent solution at the same rate removed by reaction, along with recycle of the solvent.

2. A process as claimed in claim 1, wherein the solvent has a boiling point below 100° C.

3. A process as claimed in claim 1, wherein the solvent has a boiling point below 60° C.

4. A process as claimed in any one of claims 1 to 3, wherein the quantity of solvent used is at least 10 ml per gram of TCNQ.

5. A process as claimed in any one of claims 1 to 3, wherein the quantity of solvent used is from 15 to 30 ml per gram of TCNQ.

* * * * *